(12) United States Patent
Kleiner

(10) Patent No.: US 7,288,664 B2
(45) Date of Patent: Oct. 30, 2007

(54) REVERSE KLEINER METHOD FOR MANUFACTURING NITROGEN DIOXIDE, NITRIC OXIDE, NITRIC ACID, METALLIC ASCORBATES AND ALKYL ASCORBATES OF VITAMIN C

(76) Inventor: Bela Kleiner, 2705 Kings Highway 3D, Brooklyn, NY (US) 11229

( * ) Notice: Subject to any disclaimer, the term of this patent is extended or adjusted under 35 U.S.C. 154(b) by 492 days.

(21) Appl. No.: 10/814,916

(22) Filed: Mar. 30, 2004

(65) Prior Publication Data

US 2005/0222438 A1    Oct. 6, 2005

(51) Int. Cl.
*C07D 307/34* (2006.01)

(52) U.S. Cl. ...................................... 549/315
(58) Field of Classification Search ................. 549/315
See application file for complete search history.

(56) References Cited

OTHER PUBLICATIONS

Hickman et al., Industrial & Engineering Chemistry Research (1991), 30(1), 50-5.*

* cited by examiner

Primary Examiner—Rebecca Anderson

(74) Attorney, Agent, or Firm—Bela Kleiner

(57) ABSTRACT

In this invention new chemical reactions, new chemical processes are established, and these chemical reactions, chemical processes can be used with the designed system to produce nitrogen dioxide, nitric oxide and calcium ascorbate or calcium isoascorbate.

The reaction vessel contains the aqueous ascorbic acid solution or aqueous isoascorbic acid solution. The temperature in the reaction vessel at the start of the reaction is at temp. 55° C. Into this solution is injected calcium nitrite dissolved in water. The gases generated by the chemical reactions are collected in the gas vessel.

Here two sets of chemical reactions take place; one on the surface of the solution that produces the bulk of the gas mixture. In the liquid phase, the reactions go slow; and it gives nitric acid, calcium ascorbate and nitric oxide. Instead of calcium ascorbate one can use isoascorbate, in that case the chemical reactions will go somewhat slower.

1 Claim, 4 Drawing Sheets

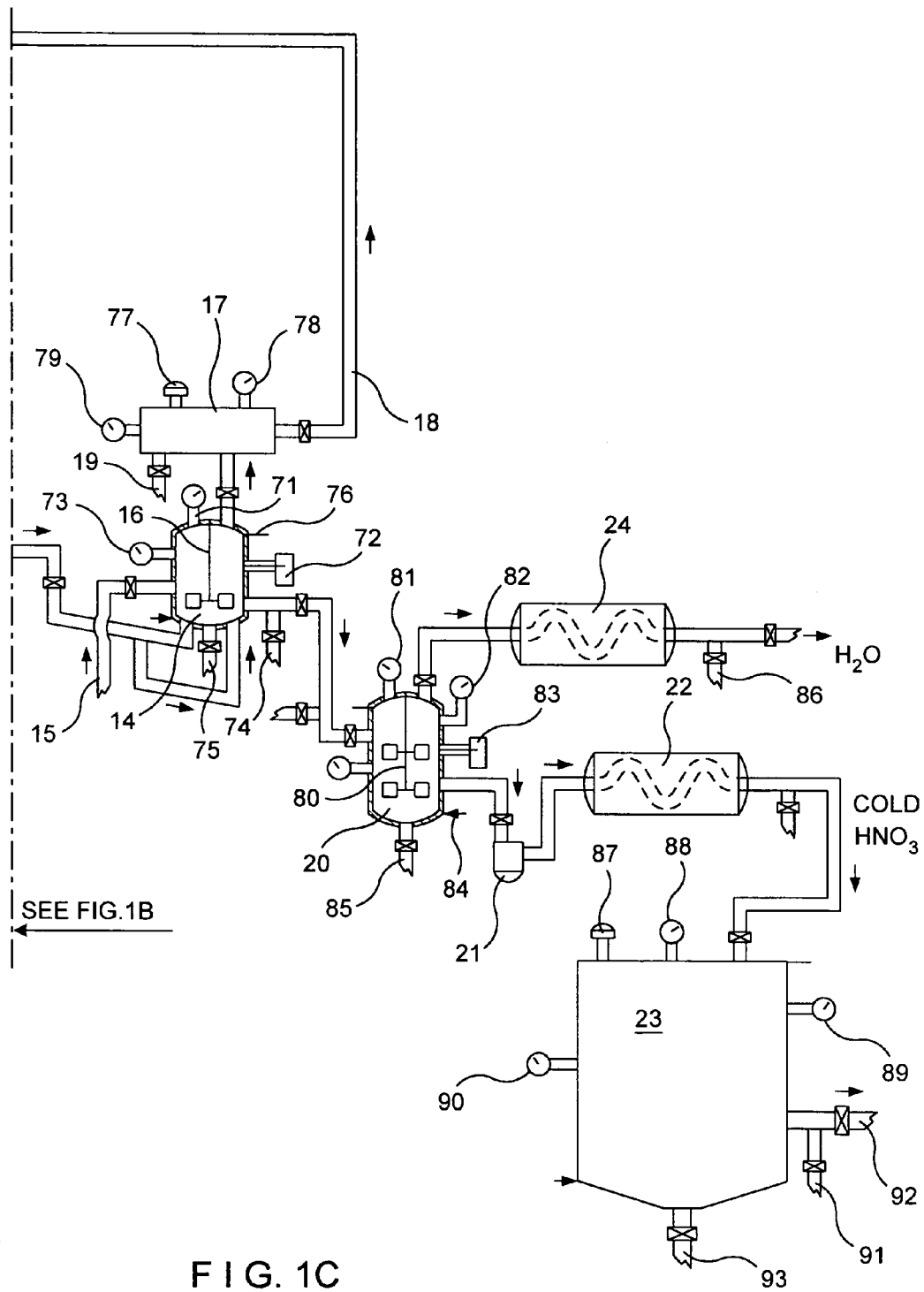
F I G. 1C

REVERSE KLEINER METHOD FOR MANUFACTURING NITROGEN DIOXIDE, NITRIC OXIDE, NITRIC ACID, METALLIC ASCORBATES AND ALKYL ASCORBATES OF VITAMIN C

This process; my invention to manufacture nitrogen dioxide, nitric oxide and nitric acid and metallic ascorbate salts as well as alkyl ascorbates: reverse Kleiner method. The major chemical reactions what my new system is concerned with, in large extent, take place on the surface of the water medium and produce two different gases; namely nitrogen dioxide and nitric oxide as well as metallic ascorbates such as: sodium ascorbate, potassium ascorbate, calcium ascorbate, barium ascorbate, silver asborbate and also alkyl ascorbates such as isobutyl ascorbate or isoamyl ascorbate. In the deeper layer of the water medium, chemical reactions also take place, those chemical reactions produce nitric acid, nitric oxide and metallic ascorbates or alkyl ascorbates, in case of using isobutyl nitrite as second reactant, isobutyl ascorbate. The nitric acid and the salt(s) formed by the chemical process, remain partially or wholly dissolved in the solution. Elevating the temperature or the pressure in the reaction vessel, the ratio of the forming two gases may shift in favor of one or the other, however, with the temperature one has to be careful. The reactant ascorbic acid is temperature sensitive as well as some of the forming products too, like calcium ascorbate.

The chemical reactions take place in the reaction vessel at room temperature or at some elevated temperature, where, on large surface area; concentrated ascorbic acid solution is loaded into the reaction vessel to form shallow pool of the solution with fairly large surface area. The system preferably should be under vacuum, however, it is not essential. The reactions still will take place whether the system is evacuated of air or not. The reactions start at room temperature, but goes better at elevated temperature. The reactions in the reaction vessel may be exothermic and they go fast, fairly fast or slow depend on what salt is chosen to run the chemical reactions with, what concentration of the ascorbic acid is or the salt solution and its concentration is used. The higher the concentration of the salt solution as well as the ascorbic acid solution, the faster the reactions. The first reactant in my invention is the ascorbic acid; the higher the concentration, the faster the reactions will go. The second reactant in my process one can choose among, what one wants harvest from the system, sodium nitrite, potassium nitrite, calcium nitrite, barium nitrite, silver nitrite and isobutyl nitrite, isoamyl nitrite etc. On the industrial scale as well as on the small scale, the best result can be achieved with sodium nitrite, potassium nitrite, calcium nitrite as well as with isobutyl nitrite. The other nitrite, because, they are not very soluble in water, yet can not give a good yield, however, at elevated temperature, they yield some product. The chemical reactions go fastest when the ascorbic acid is at its maximum concentration and at elevated tempetature about 55 centigrade. When this process uses inorganic metallic salts, the chemical reactions probably go fastest with potassium nitrite, second fastest with sodium nitrite, goes fast with calcium nitrite, slow with barium nitrite, very slow with silver nitrite, isoamyl nitrite and isobutyl nitrite. Isobutyl nitrite, with time and good agitation, gives a very good yield. The chemical reactions with calcium nitrite would go much faster, but because it contains too much water that makes the chemical reactions go much slower. Alkyl nitrites are not very stable compounds, only the fresh ones will give a good yield. In my invention on the surface of the ascorbic acid solution pool, and in the solution medium the following chemical reactions are taking place:

1. when sodium nitrite ($NaNo_2$) is used as the second reactant:
(I) on the surface on the solution pool
  a., main chemical reaction path

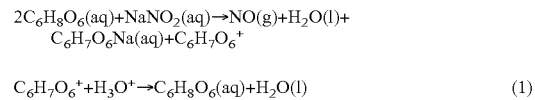

$$C_6H_7O_6^+ + H_3O^+ \rightarrow C_6H_8O_6(aq) + H_2O(l) \tag{1}$$

b., competing chemical reaction path I

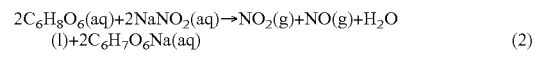

c., competing chemical reaction path II

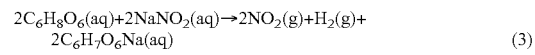

here the gases collect above the surface of the solution.
(II). in the liquid phase of the ascorbic acid solution

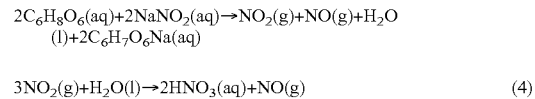

$$3NO_2(g) + H_2O(l) \rightarrow 2HNO_3(aq) + NO(g) \tag{4}$$

In the liquid phase, the nitrogen dioxide that formed, immediately reacts with water and thus forms nitric acid and nitric oxide.

2. when potassium nitrite ($KNO_2$) is used as the second reactant:
(I) on the surface of the solution pool
  a., main chemical reaction path

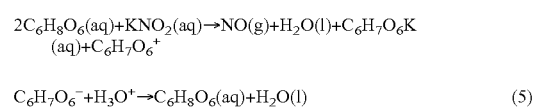

$$C_6H_7O_6^- + H_3O^+ \rightarrow C_6H_8O_6(aq) + H_2O(l) \tag{5}$$

b., competing chemical reaction path I

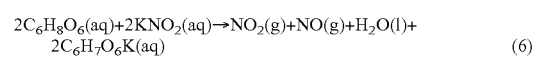

c., competing chemical reaction path II

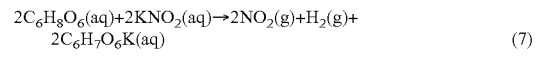

(II) in the liquid phase of the ascorbic acid solution

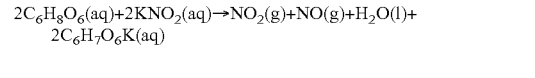

$$3NO_2(g) + H_2O(l) \rightarrow 2HNO_3(aq) + NO(g) \tag{8}$$

3. when calcium nitrite ($Ca(NO_2)_2$) is used as the second reactant:
(I) on the surface of the solution pool
  a., main chemical reaction path

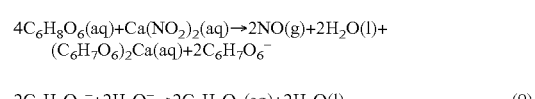

$$2C_6H_7O_6^- + 2H_3O^- \rightarrow 2C_6H_8O_6(aq) + 2H_2O(l) \tag{9}$$

b., competing chemical reaction path I

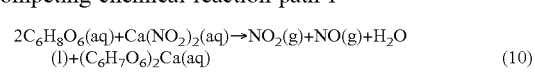

c., competing chemical reaction path II

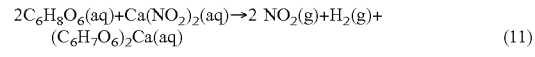

(II) in the liquid phase of the ascorbic acid solution $$2C_6H_8O_6(aq)+Ca(NO_2)_2(aq)\rightarrow NO_2(g)+NO(g)+H_2O(l)+(C_6H_7O_6)_2Ca(aq)$$

$$3NO_2(g)+H_2O(l)\rightarrow 2HNO_3(aq)+NO(g) \quad (12)$$

4. when barium nitrite $Ba(NO_2)_2$ is used as the second reactant:
(I) on the surface of the ascorbic acid solution pool
a., main chemical reaction path $$4C_6H_8O_6(aq)+Ba(NO_2)_2(aq)\rightarrow 2NO(g)+2No(g)+2H_2O(l)+(C_6H_7O_6)_2Ba(aq)+2C_6H_7O_6^-$$

$$2C_6H_7O_6^-+2H_3O^+\rightarrow 2C_6H_8O_6(aq)+2H_2O(l) \quad (13)$$

b., competing chemical reaction path I $$2C_6H_8O_6(aq)+Ba(NO_2)_2(aq)\rightarrow NO_2(g)+NO(g)+2H_2O(l)+(C_6H_7O_6)_2Ba(aq) \quad (14)$$

c., competing chemical reaction path II $$2C_6H_8O_6(aq)+Ba(NO_2)_2(aq)\rightarrow 2NO_2(g)+H_2(g)+(C_6H_7O_2)Ba(aq) \quad (15)$$

(II) in the liquid phase of the ascorbic acid solution $$2C_6H_8O_6(aq)+Ba(NO_2)_2(aq)\rightarrow NO_2(g)+NO(g)+H_2O(l)+(C_6H_7O_6)_2Ba(aq)$$

$$3NO_2(g)+H_2O(l)\rightarrow 2HNO_3(aq)+NO(g) \quad (16)$$

5. when silver nitrite $(AgNO_2)$ is used as second reactant:
(I) on the surface of the ascorbic acid solution pool
a., main chemical reaction path $$2C_6H_8O_6(aq)+2AgNO_2(aq)\rightarrow NO_2(g)+NO(g)+H_2O(l)+2C_6H_8O_6Ag(s) \quad (17)$$

b., competing chemical reaction path I $$2C_6H_8O_6(aq)+2AgNO_2(aq)\rightarrow NO_2(g)+H_2(g)+2C_6H_8O_6Ag(s) \quad (18)$$

(II) in the liquid phase of the ascorbic acid solution $$2C_6H_8O_6(aq)+2AgNO_2(aq)\rightarrow NO_2(g)+NO(g)+H_2O(l)+2C_6H_7O_6Ag(s)$$

$$3NO_2(g)+H_2O(l)\rightarrow 2HNO_3(aq)+NO(g) \quad (19)$$

6. when isobutyl nitrite is used as the second reactant:
(I) on the surface of the ascorbic acid solution pool
a., main chemical reaction path $$2C_6H_7O_6(aq)+2C_4H_9NO_2(l)\rightarrow 2NO(g)+C_6H_7O_6C_4H_9(aq)+C_6H_7O_6^-+C_4H_9OH(l)$$

$$C_6H_7O_6^-+H_3O^+\rightarrow C_6H_8O_6(aq)+H_2O(l) \quad (20)$$

b., competing chemical reaction path I $$2C_6H_8O_6(aq)+2C_4H_9NO_2(l)\rightarrow NO_2(g)+NO(g)+H_2O(l)+2C_6H_7O_6C_4H_9(aq) \quad (21)$$

(II) in the liquid phase of the ascorbic acid solution $$2C_6H_8O_6(aq)+C_4H_9NO_2(aq)\rightarrow NO_2(g)+NO(g)+H_2O(l)+2C_6H_7O_6C_4H_9(aq)$$

$$3NO_2(g)+H_2O(l)\rightarrow 2HNO_3(aq)+NO(g) \quad (22)$$

With isobutyl nitrite as the second reactant; other chemical reactions take place here in this medium, however, those chemical reactions are not understood yet.
7. when isoamyl nitrite is used as the second reactant:
(I) on the surface of the ascorbic acid solution pool
a., main chemical reaction path $$2C_6H_8O_6(aq)+2C_5H_{11}NO_2(l)\rightarrow 2NO(g)+C_6H_7O_6C_5H_{11}(aq)+C_6H_7O_6^-+C_5H_{11}OH(l)$$

$$C_6H_7O_6^-+H_3O^+\rightarrow C_6H_8O_6(aq)+H_2O(l) \quad (20)$$

b., competing chemical reaction path I $$2C_6H_8O_6(aq)+2C_5H_{11}NO_2(l)\rightarrow NO_2(g)+NO(g)+H_2O(l)+2C_6H_7O_6C_5H_{11}(aq) \quad (21)$$

(II) in the liquid phase of the ascorbic acid solution $$2C_6H_8O_6(aq)+C_5H_{11}NO_2(aq)\rightarrow NO_2(g)+NO(g)+H_2O(l)+2C_6H_7O_6C_5H_{11}(aq)$$

$$3NO_2(g)+H_2O(l)\rightarrow 2HNO_3(aq)+NO(g) \quad (22)$$

With isoamyl nitrite as the second reactant; other chemical reactions take place here in this medium, however, those chemical reactions are not understood yet.
8. when isopropyl nitrite is used as the second reactant:
(I) on the surface of the ascorbic acid solution pool
a., main chemical reaction path $$2C_6H_8O_6(aq)+2C_3H_7NO_2(l)\rightarrow 2NO(g)+C_6H_7O_6C_3H_7(aq)+C_6H_7O_6^-+C_3H_7OH(l)$$

$$C_6H_7O_6^-+H_3O\rightarrow C_6H_8O_6(aq)+H_2O(l) \quad (20)$$

b., competing chemical reaction path I $$2C_6H_8O_6(aq)+2C_3H_7NO_2(l)\rightarrow NO_2(g)+NO(g)+H_2O(l)+2C_6H_7O_6C_3H_7(aq) \quad (21)$$

(II) in the liquid phase of the ascorbic acid solution $$2C_6H_8O_6(aq)+C_3H_7NO_2(aq)\rightarrow NO_2(g)+NO(g)+H_2O(l)+2C_6H_7O_6C_3H_7(aq)$$

$$3NO_2(g)+H_2O(l)\rightarrow 2HNO_3(aq)+NO(g) \quad (22)$$

With isopropyl nitrite as the second reactant; other chemical reactions take place here in this medium, however, those chemical reactions are not understood yet. Isopropyl nitrite is very unstable and dangerous; in the product propyl aldehyde also may form, however, that is not so dangerous, because there it will be in aqueous solution. This reaction was not performed. The chemical reactions are started in the reaction vessel by spraying the second reactant(s); the nitrite salt on the surface of the shallow, ascorbic acid solution pool. The spraying is done with some force, so that the nitrite drops hit the surface of the solution pool with some velocity. The nitrite salt solution, the more concentrated, the better. The nitrite salt solution is about 42% concentration. The ascorbic acid concentration has the optimal concentration that is close to saturation point that gives the best result concerning producing the two gases: nitrogen dioxide and nitric oxide. The chemical reactions will proceed well at room temperature, however, at elevated temperature the chemical reactions will go faster. Nevertheless there is an optimal temperature at which ascorbic acid reacting with nitrite salt will give the best result. Some temperature develops during the reaction run. In large scale reaction runs, the temperature of the reaction vessel has to be maintained. When the reaction starts, the liberated gas mixture (nitrogen dioxide and nitric oxide) collects above the surface of the solution and fills the reaction vessel, then the gas mixture drifts over into the gas tank or if the gas-converter is used, the gas mixture is sucked away into the gas converter to allow the least amount of the generated nitrogen dioxide to dissolve into the ascorbic acid solution. The amount of the second reactant is delivered into the reaction vessel to the amount to try to exhaust the concentration of the ascorbic acid to the last molecule if possible, however, the chemical reactions have their own lives here that govern how far the chemical reactions will go. The amount of the reactants can be brought together stoichiometrically when the yield of the reaction harvest is not the priority attainment. In the gas tank the gas mixture which consists of nitrogen dioxide and nitric oxide and some impurities can be converted into homogenous nitrogen dioxide by introducing oxygen into the tank. The oxygen will react with the nitric oxide to form nitrogen dioxide $$2NO(g) + O_2(g) \rightarrow 2NO_2(g) \tag{23}$$

For this same conversion air also can be used, the oxygen contained in air will react with nitric oxide giving nitrogen dioxide, however, this approach is less efficient.

Now the homogenous nitrogen dioxide in the gas tank can be used as the final product on one hand or it can be transferred into the acid converter there the gas is mixed with water, thus it converts into nitric acid; reacts with water and forms nitric acid.

In the acid converter the collected and converted nitrogen dioxide gas is bubbled into water; here the $NO_2$ gas reacts with water forming nitric acid and nitric oxide as follow:

$$3NO_2(g) + H_2O(l) \rightarrow 2HNO_3(aq) + NO(g) \tag{24}$$

From the acid converter nitric oxide gas that has formed there is transferred into the nitrogen-oxide tank and collected there as the final product or it can be recycled back into the system either into the gas tank when the system is designed for the gas tank or into the gas-converter if the system is designed for gas converter. From the acid converter, the row nitric acid solution is transferred into the distilling vessel where the excess water is distilled off, then the concentrated nitric acid goes through a cooler into the nitric acid product tank.

The secondary products from the reaction vessels are transferred into the secondary distilling vessel; here the secondary products are indeed, at least some of the very important products. The important secondary products are sodium ascorbate, potassium ascorbate, calcium ascorbate. Less important are barium ascorbate, silver ascorbate and isobutyl ascorbate. All these secondary products to be isolated and recovered, each needs to be treated differently. In the chemical reaction run, no matter which nitrite salt is used, the ascorbic acid reactant can not be exhausted fully; with the sodium nitrite, potassium nitrite and calcium nitrite use as second reactant, the remaining ascorbic acid reactant present in the solution can be converted to sodium ascorbate by adding sodium bicarbonate to the solution transferred into the secondary distilling vessel. The same can be done when potassium nitrite is used as the second reactant, however, here potassium bicarbonate is used to convert the remaining ascorbic acid to potassium ascorbate. With calcium nitrite is used as second reactant, calcium carbonate—converting the remaining, unreacted ascorbic acid to calcium ascorbate—is used. Here the secondary distilling vessel serves as the secondary reactor where the following chemical reactions take place either at room temperature or at a little higher temperature; between 40 to 60 centigrade.

$$C_6H_8O_6(aq) + NaHCO_3(aq) \rightarrow C_6H_7O_6Na(aq) + H_2O(l) + CO_2(aq) \tag{25}$$

and $$C_6H_8O_6(aq) + KHCO_3(aq) \rightarrow C_6H_7O_6K(aq) + H_2O(l) + CO_2(g) \tag{32}$$

With calcium nitrite used as second reactant $$2C_6H_8O_6(aq) + CaCO_3(s) \rightarrow (C_6H_7O_6)_2Ca(aq) + H_2O(l) + CO_2(g) \tag{33}$$

Sodium bicarbonate or potassium bicarbonate or calcium carbonate is added to the solution in the secondary distilling vessel to some excess to the stoichiometric quantity of the ascorbic acid still remaining, unreacted in the solution. Then some of the liquid of the solution can be stripped off here in the secondary distilling vessel, however, only gently, then the secondary products in the secondary distilling vessel are transferred into the settling tank. In the settling tank the sodium ascorbate or the potassium ascorbate or calcium ascorbate is left to precipitate from the solution then. The product precipitation may take some time, for the potassium ascorbate the precipitation time is even longer than for the sodium ascorbate, for potassium ascorbate, it may take days. With these crude sodium ascorbate and potassium ascorbate, but also with all the metallic ascorbates one has to be careful, they have to be stabilized before they can be collected, otherwise they will deliquesce; water will not stabilize them, only the solution in which they are made.

The procedures for the secondary products resulting from the reactions using the second reactant as calcium nitrite, barium nitrite, silver nitrite or isobutyl nitrite, secondary distilling vessel is not used as a secondary reaction vessel, running the chemical reactions with these eforementioned nitrites, secondary reaction using sodium bicarbonate or potassium bicarbonate would result in a mixture of different metallic ascorbates that may be hard to separate from each other, thus the secondary products resulting from using, barium nitrite or isobutyl nitrite as the second reactant, the solution from the reaction vessel is transferred to the secondary distilling vessel, there some of the liquid is tripped off of the solution but gently, then the solution containing the secondary product(s) is transferred into the settling tank; sodium ascorbate, potassium ascorbate, calcium ascorbate, barium ascorbate, isobutyl ascorbate, isoamyl ascorbate will precipitate out of the solution. Again, it may take some time; then the solid metallic ascorbates as well as isobutyl ascorbate, isoamyl ascorbate can be collected, further purified and used for many purposes.

If the crude ascorbates, the secondary products from the chemical processes are left to dry, these ascorbates, as liquids evaporate, they will form brown cakes; as the cakes dry further, the cake will crumble; some gases develop inside these cakes; these gases probably are oxygen, carbon dioxide and maybe some nitric oxide and nitrogen dioxide, but these nitrogen oxides are unlikely.

If the system is designed with the gas converter where the gas mixture of the nitrogen dioxide and nitrogen oxide is drawn away from the reaction vessel can be mixed with oxygen under pressure, thus NO gas converts into nitrogen dioxide and then the process can be employed that has been used at the use of the gas tank.

Sodium ascorbate, potassium ascorbate and calcium ascorbate; after the final chemical reactions—converting the remaining unreacted ascorbic acid reactant to product—is over; these ascorbates; sodium ascorbate, potassium ascorbate, calcium ascorbate can be collected faster by precipitating these metallic ascorbates with alcohol; namely 2-propanol.

I'll describe these procedures separately, because, to obtain any of the above mentioned products, require different and specific approaches in their productions.

Sodium ascorbate as a secondary product is produced when the system uses ascorbic acid and sodium nitrite as reactants. It gives a good result in regard of generating the gases; nitrogen dioxide and nitric oxide as well as sodium ascorbate when the reaction temperature is maintained at 55° C. This formed sodium ascorbate can be left to precipitate from the mother liquid, but then, it has to be separated from the liquid after some time that the unreacted sodium nitrite contained in the mother liquid will not precipitate out with the product, sodium ascorbate or when here the final chemical reactions—converting the remaining, unreacted ascorbic acid to sodium ascorbate—is over, one can add 2-propanol to the reaction solution in a ratio 2 ml 2-propanol to 1 ml reaction solution or the ratio can be a little higher in favor of 2-propanol.

Adding the 2-propanol, two solution layers will form. The bottom layer solution is black; it contains most of the sodium ascorbate product; the top layer is yellowish; it may contain some of the sodium ascorbate product.

These two solution layers can be easily separated and transferred into two different containers. To the dark solution water is added and from this solution will precipitate out—after some time—the product, sodium ascorbate; it can then be further washed and purified. The top layer can be checked for products, then treated as waste. Potassium ascorbate as a secondary product is produced when the system uses ascorbic acid and potassium nitrite as reactants. It gives a good result in regard of generating the gases; nitrogen dioxide and nitric oxide as well as potassium ascorbate when the reaction temperature is maintained at 55° C. This formed potassium ascorbate can be left to precipitate from the mother liquid, but then, it has to be separated from the liquid after some time that the unreacted potassium nitrite contained in the mother liquid will not precipitate out with the product, potassium ascorbate or when here the final chemical reactions—converting the remaining, unreacted ascorbic acid to potassium ascorbate—is over, one can add 2-propanol to the reaction solution in a ratio 2 ml 2-propanol to 1 ml reaction solution or the ratio can be a little higher in favor of 2-propanol.

Adding the 2-propanol, two solution layers will form. The bottom layer solution is black; it contains most of the potassium ascorbate product; the top layer is yellowish; it may contain some of the potassium ascorbate product.

These two solution layers can be easily separated and transferred into two different containers. From the dark solution will settle out—after some time—the product, potassium ascorbate; it can then be further washed and purified. The top layer can be checked for products, then treated as waste.

Potassium ascorbate is hard to precipitate. One can do to harvest the potassium ascorbate as a mixture of potassium ascorbate and sodium ascorbate. This mixture will be a little easier to precipitate from the solution. Here at the last reaction step when the remaining, unreacted ascorbic acid is converted to potassium ascorbate, instead of adding potassium bicarbonate one adds sodium bicarbonate. This step will add some sodium ascorbate to the already formed potassium ascorbate, also some potassium ascorbate may convert to sodium ascorbate, but as a product harvest, it'll be a mixture of potassium- and sodium ascorbates. In the mother liquid still will remain some potassium ascorbate.

Calcium ascorbate as a secondary product is produced when the system uses ascorbic acid and calcium nitrite as reactants, however, here the reaction temperature must be lowered to about 25° C. otherwise the chemical reactions will result in dye stuff that presently I do not know what that may be. Of course the gas mixture at lower temperature will be less, yet It gives a good result in regard of generating the gases; nitrogen dioxide and nitric oxide as well as calcium ascorbate when the reaction temperature is maintained at 25° C. This formed calcium ascorbate can be left to precipitate from the mother liquid, but then, it has to be separated from the liquid after some time that the unreacted calcium nitrite contained in the mother will not precipitate out with the product, calcium ascorbate or when here the final chemical reactions—converting the remaining, unreacted ascorbic acid to calcium ascorbate—is over, some water is added to the solution; then the solution is filtered. The yellow precipitate and the remaining non-reacted calcium carbonate remains on the filter bed. This yellow precipitate may contain some calcium ascorbate. This yellow solid is collected from the filter then and the calcium ascorbate may further be extracted from it. To this dark liquid one can add 2-propanol in a ratio 3 ml 2-propanol to 1 ml reaction solution or the ratio can be a little higher in favor of 2-propanol. At this point brown, spongy substance, not much, will sink to the bottom of the solution; it is sticky, it is almost like tar. This tar-like stuff is removed from the tank. The top solution is brownish and a little whitish. This solution remains in the tank and to this 2-propanol-water reaction solution is added absolute or 95% ethanol in ratio 2 ml ethanol to 1 ml solution. After some time, slowly but surely white calcium ascorbate as white, curdy substance will precipitate from the solution. This solution is transferred to the ascorbate-filtering tank. The solution is filtered, the white precipitate is washed with absolute ethanol. This substance is very delicate, it will deliquesce into the air, so it should be stabilized in the alcoholic solution for some time, then it should be collected under inert gas. The filtrate, still contains some calcium ascorbate, is collected in the ascorbate-filtering tank and the product, calcium ascorbate is further extracted, so the filtrate is transferred back into the alcohol-mixing tank, there is added absolute alcohol in ratio 2 ml alcohol to 1 ml solution. This mixture is mixed well and again the white calcium ascorbate will precipitate out of the solution. Again it is transferred into the ascorbate-filtering tank, and the same is done with it as before. The collected calcium ascorbate then can be further purified. The filtrate now goes into the collecting tank or to the recovery system where 2-propanol and ethanol can be recovered.

FIELD OF THE INVENTION

My invention is a new method to manufacture nitrogen dioxide, nitric oxide and then nitric acid as well as sodium ascorbate, potassium ascorbate, calcium ascorbate, barium ascorbate, silver ascorbate, isobutyl ascorbate, isoamyl ascorbate, isopropyl ascorbate not using gases as the starting materials but as aqueous solution of ascorbic acid and the chosen nitrite solution—as is the case with isobutyl nitrite, isoamyl nitrite, isopropyl nitrite—or nitrite salt solution.

BACKGROUND OF THE INVENTION

Industrial manufacture of nitric acid is based on Ostwald process that is a century old. My invention uses new chemical processes that first yields a gas mixture that consists mostly of nitrogen dioxide and nitric oxide; these gases then are converted into nitric acid. In the prior art, nitric acid is mainly produced by the Ostwald method. Here ammonia at high pressure and temperature reacts with oxygen, the reaction produces nitric oxide. This nitric oxide is reacted again, at room temperature with oxygen, and this reaction produces nitrogen dioxide. Nitrogen dioxide is then dissolved in water that yield nitric acid solution. The water from the nitric acid is distilled off and the remaining solution becomes concentrated nitric acid. This process requires expensive catalyst, expensive reactor vessel, energy. The other method to manufacture nitric acid is the alchemist's method. Nitrate salt is dissolved in sulfuric acid, in the liquid mixture nitric acid is formed. Nitric acid is then distilled off of the sulfuric acid.

The third method to manufacture nitric acid is by the Kleiner method that is a resent invention to produce nitric acid on industrial as well as on laboratory scale. This fourth; manufacturing nitric acid out of vitamin C (ascorbic acid) is again a totally new invention. Here solid ascorbic acid is dissolved in water and brought into contact with nitrite salt solution(s). My invention does not need any catalyst, high temperature or high pressure, it does not need the nitrate salt to be soaked in sulfuric acid. The manufacture of nitric acid by reverse Kleiner method is different, even from my previous invention, besides nitric acid, by this reverse Kleiner method, one may produce important secondary products as potassium ascorbate, sodium ascorbate, calcium ascorbate barium ascorbate, silver ascorbate or isobutyl ascorbate or isoamyl ascorbate as well. The production of nitric acid by reverse Kleiner method, here the chemical reactions take place at room temperature or at some elevated temperature, it depends which nitrite is used, for the silver nitrite, the temperature will be much higher; under vacuum or at atmospheric or may be at some higher pressure, however, the pressure has the effect on the ratio of the two gases produced during the reaction run.

Manufacture of nitric acid, nitrogen dioxide, nitric oxide by this invention, can be easily done on very small, small as well as on industrial scale and conveniently produce, at the same time, useful ascorbate compound(s). I have to mention here; on the industrial scale using silver nitrite as the second reactant to produce the gases; nitrogen dioxide and nitric oxide is not feasible unless the remaining ascorbic acid in the system is not converted into other metallic ascorbate.

In my invention the first step in producing nitric acid is really the major difference of the conventional manufacturing of nitric acid, and the chemical reactions take place in the reaction vessel, there two different chemical reaction processes take place there; on the surface area of the ascorbic acid solution pool, mostly the gases are produced; nitrogen dioxide and nitric oxide. In the solution phase of the chemical reactions come into existence nitric acid, nitric oxide and the metallic ascorbate(s).

In the prior art nitric oxide is produced as mentioned earlier by oxidation of ammonia using expensive catalyst and the resent invention, the Kleiner method uses metallic nitrite solution reacting with liquid inorganic- or organic acid.

On a laboratory scale pure copper is dissolved in nitric acid; this process produces nitric oxide; this nitric oxide may then be reacted with oxygen or air yielding then nitrogen dioxide. In my invention in one step two gases; nitrogen dioxide, nitric oxide are produced 1:1 or, so ratio, and also the secondary products as sodium ascorbate, potassium ascorbate, calcium ascorbate, barium ascorbate, silver ascorbate, isobutyl ascorbate, isoamyl ascorbate, depends which nitrite salt solution is used as the second reactant. If higher then atmospheric pressure is used, higher pressure may favor nitrogen dioxide formation to a certain amount. This ratio is influenced also by the concentration of the reactants too.

Pouring dilute nitric acid on iron filing will yield some nitric oxide.

In the prior art nitrogen dioxide is produced by reacting the nitric oxide obtained from a previous process. Also In my invention the two gases produced either can be separated or one turned into the other and used for producing nitric acid or both can be used as final products. These gases generated by using ascorbic acid solution reacting with nitrite solution which is my newest invention, can be easily produced on a small or on a large scale, it does not need sophisticated equipments; it is safe and very efficient.

In the prior art calcium ascorbate is manufactured by the Ruskin method; U.S. Pat. No. 2,596,103 (1952) and sodium ascorbate by the Holland method; U.S. Pat. No. 2,442,005 (1948).

BRIEF SUMMARY OF THE INVENTION

My invention establishes new chemical processes to produce, manufacture nitrogen dioxide, nitric oxide and finally nitric acid as well as different metallic ascorbates and alkyl ascorbates on industrial as well as on very small scale without using any catalyst, high temperature or pressure. In these processes the starting materials are liquids and not gases. In these chemical processes the chemical reactions in the reaction vessel take place at two places, on the surface of the solution and in the solution phase, in the liquid.

When ascorbic acid is dissolved in water at certain concentration and it comes into contact with the second reactant; either sodium nitrite, potassium nitrite, calcium nitrite, barium nitrite, silver nitrite aqueous solution or isobutyl nitrite or isoamyl nitrite or isopropyl nitrite liquid. At certain concentration of the reactants, chemical reactions will take place. From the surface reactions come nitrogen dioxide and nitric oxide, and some impurity gases, plus the metallic ascorbates or alkyl ascorbates.

The chemical reactions in the solution phase will yield first nitrogen dioxide that then dissolves into solution and forms nitric acid, nitric oxide, metallic ascorbate(s) such as sodium-, potassium-, calcium-, barium-, silver- or isobutyl ascorbate or isoamyl ascorbate and water.

The chemical reactions take place at room temperature or at some elevated temperature and either under vacuum or at atmospheric pressure. Here two sets of chemical reactions go on; one on the surface of the solution, the other; in the solution, liquid phase.

The object of my invention is: to devise easier method to manufacture nitrogen dioxide, nitric oxide and nitric acid on large, industrial scale as well as on small, laboratory scale and at the same time produce most desired metallic ascorbates.

BRIEF DESCRIPTION OF DRAWINGS

FIG. 1C shows the system for manufacturing nitrogen dioxide, nitric oxide, nitric acid, metallic ascorbates and alkyl ascorbates of vitamin C.

DETAILED DESCRIPTION OF MY INVENTION

Figure 1:
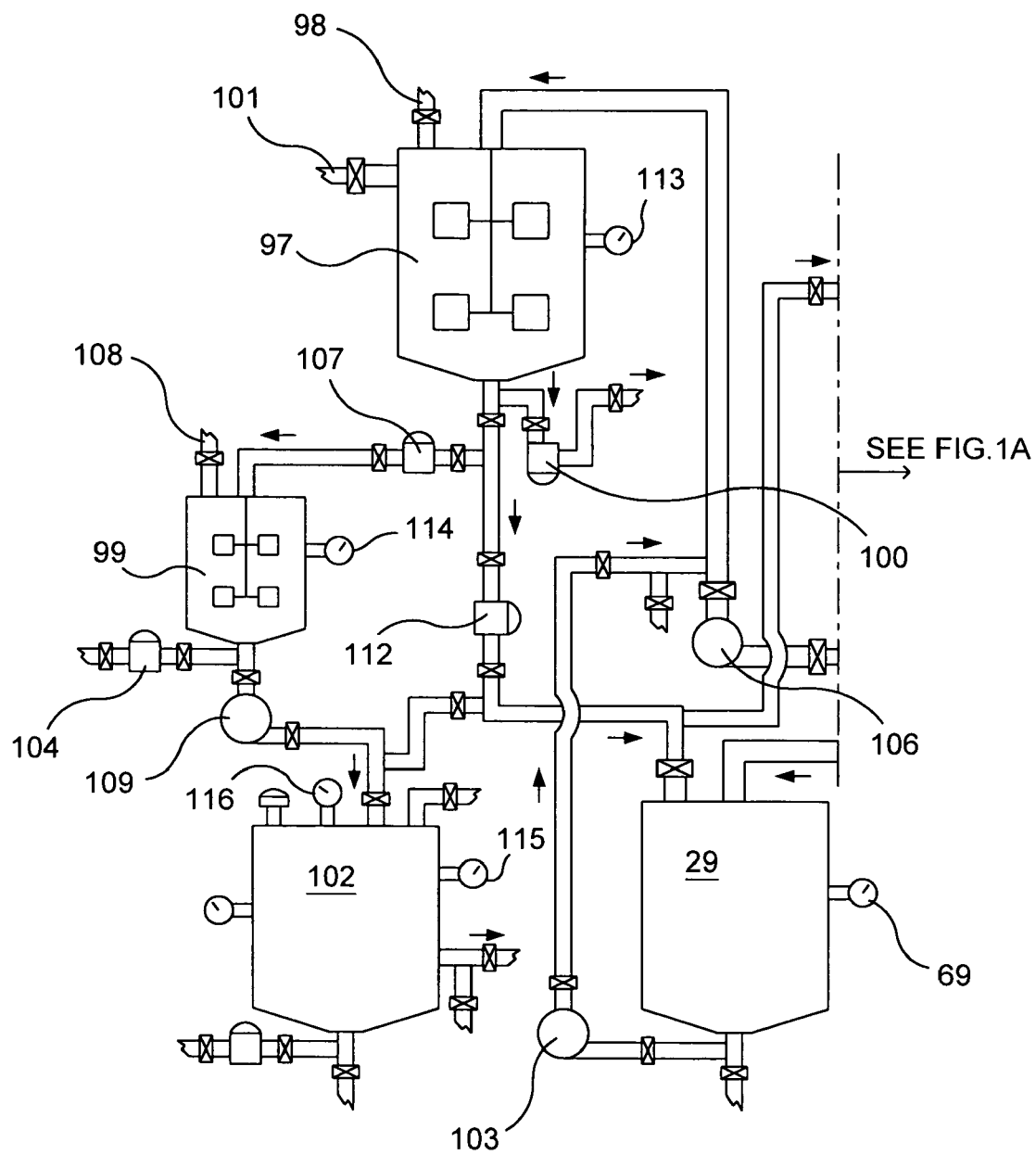
FIG. 1 shows the system for manufacturing nitrogen dioxide, nitric oxide, nitric acid, metallic ascorbates and alkyl ascorbates of vitamin C.
Figure 1A:
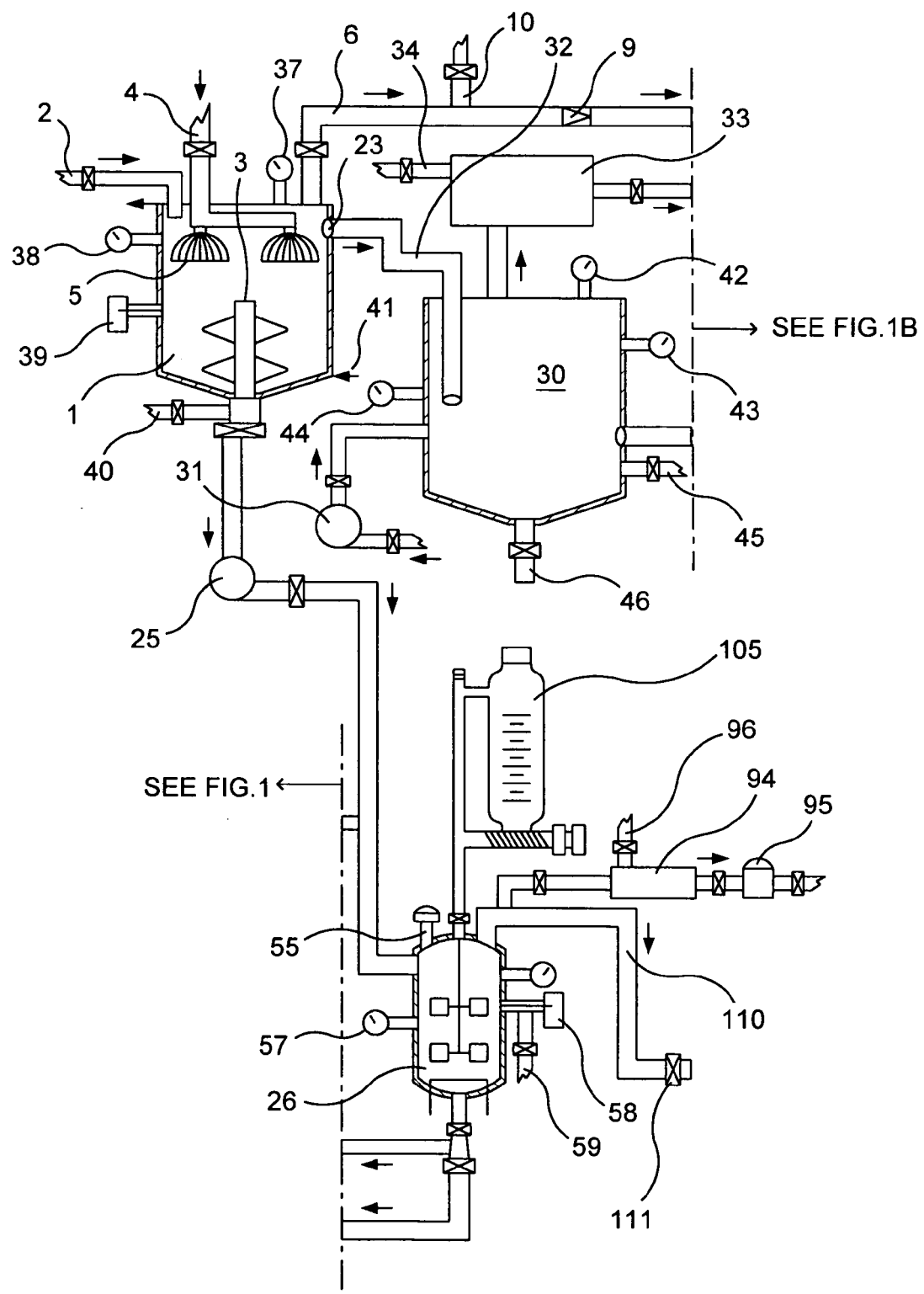
FIG. 1A shows the system for manufacturing nitrogen dioxide, nitric oxide, nitric acid, metallic ascorbates and alkyl ascorbates of vitamin C.
Figure 1B:
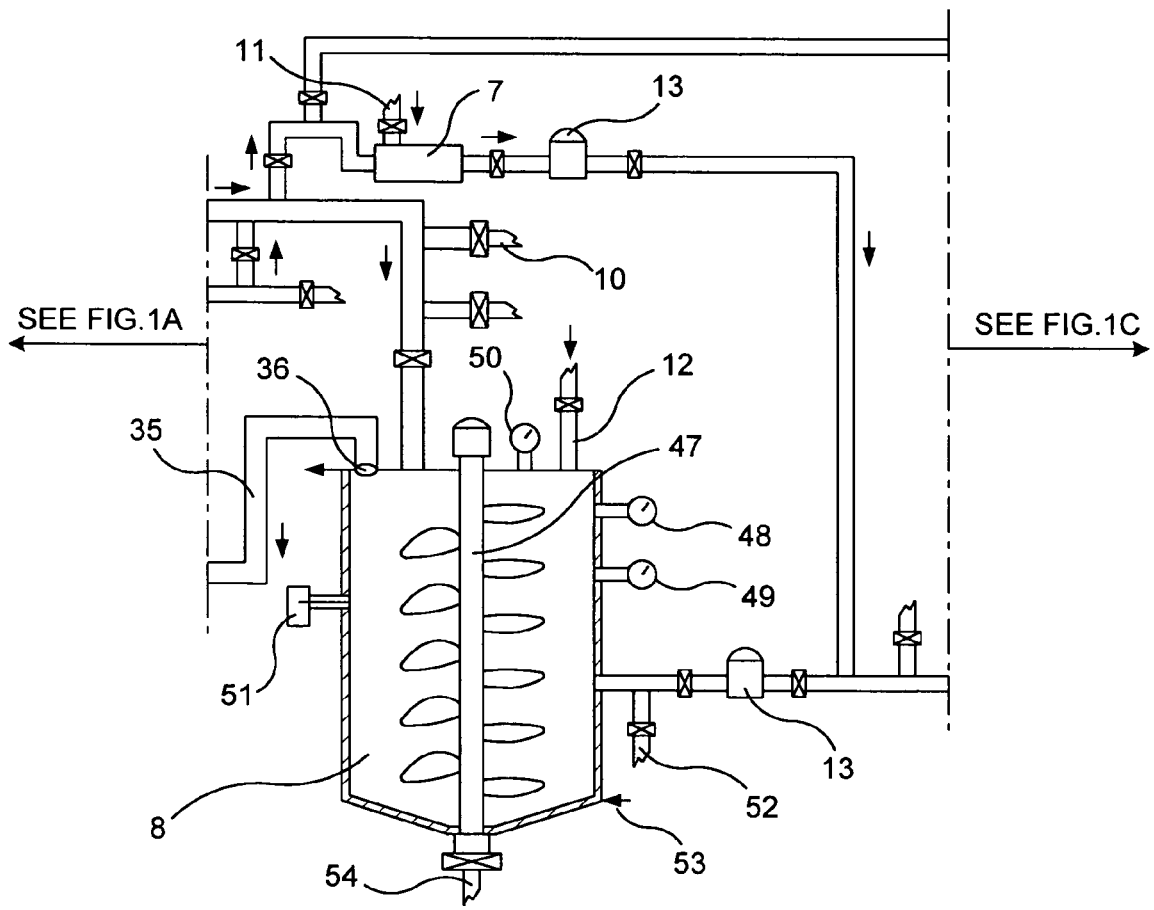
FIG. 1B shows the system for manufacturing nitrogen dioxide, nitric oxide, nitric acid, metallic ascorbates and alkyl ascorbates of vitamin C.

My invention is a new method to manufacture nitrogen dioxide, nitric oxide, nitric acid metallic ascorbates and alkyl ascorbates, however, to manufacture nitric acid, I need to obtain the row material, nitrogen dioxide for it. I have to start from a different prospective as conventional; known manufacturing processes do. I'm not using the oxidation of ammonia to obtain the nitrogen oxides as most of the manufacturing processes of nitric acid employ. These chemical processes in my invention could be treated separately, however, the chemical reactions of these processes take place almost at the same time in that defined area and because the final products are the results of the first step of these chemical processes my invention uses without which none of the products, in these processes, could come into existence. To produce nitric acid, I need to obtain the row material, nitrogen dioxide; for that I am not using the Ostwald process. I've discovered a method to get the nitrogen dioxide gas from other source. In my invention I use sodium nitrite or potassium nitrite as well as other nitrites as the source for obtaining nitrogen dioxide. The nitrite salt is dissolved in water almost to its saturation point (about 42% by weight), and applying surface reaction; using a shallow pool of ascorbic acid dissolved in water in certain concentration and spraying onto the surface of the ascorbic acid solution pool the second reactant either sodium nitrite, potassium nitrite, calcium nitrite, barium nitrite, silver nitrite disssolved in water or liquid isobutyl nitrite or isoamyl nitrite, with some force. The chemical reactions between the reactants, on the surface of the solution pool, produce nitrogen dioxide and nitric oxide. The reactions take place in the reaction vessel, at room temperature or at some elevated temperature. The reactions can be started under vacuum or at atmospheric pressure. In the reaction vessel, on the surface of the shallow pool of the ascorbic acid solution, as the second reactant, the nitrite solution; nitrite mist, nitrite solution droplets hit the surface of the solution of the ascorbic acid with some velocity, chemical reactions take place. The reactions go fast with potassium nitrite, sodium nitrite, calcium nitrite, barium nitrite, slow with silver nitrite and isobutyl nitrite and isoamyl nitrite. Isobutyl nitrite and isoamyl nitrite, because it is not very miscible with water solution, the chemical reactions go much slower. On the surface of the solution the gas mixture; nitrogen dioxide, nitric oxide and some impurities will collect; the metallic ascorbate, alkyl ascorbate which forms at the chemical reactions will remain in the solution as ions or settles out on the bottom of the reaction vessel as solid, as is the case with silver ascorbate, also some nitrogen dioxide dissolves into the solution and forms nitric acid there. In the solution phase, in the liquid, the same or almost the same chemical reactions are taking place; the formed nitrogen dioxide, however, dissolves into the solution in the solution phase; the journey is too long for it to come up onto the surface of the solution; it does hot have the energy for that.

My invention enable to use a dozen of different nitrites to be used to produce nitrogen dioxide, nitric oxide and nitric acid, and other secondary but useful products that depends upon the second reactant used in the chemical reaction run. Whatever nitrite salt is used as the second reactant, the chemical reactions; on the surface of the solution pool, always will produce nitrogen dioxide and nitric oxide and the metallic asborbate or alkyl ascorbate; in the liquid phase always will be some nitric acid, nitric oxide produced and a metallic ascorbate or alkyl ascorbate of the metallic nitrite or of the alkyl nitrite used as the second reactant. No matter which nitrite is used, always two sets of chemical reactions take place; on the surface of the solution the chemical reactions yield nitrogen dioxide and major part of the nitric oxide; in the liquid phase, nitrogen dioxide and nitric oxide are formed; nitrogen dioxide then dissolves into the solution to form nitric acid, nitric oxide which then bubbles up onto the surface, the metallic ascorbate or alkyl ascorbate and of course, water; these will remain in the solution except silver ascorbate, when silver nitrite is used as the second reactant; silver ascorbate precipitates immediately. Metallic ascorbates as well as alkyl ascorbates will remain in the solution as ions.

From this first step of the chemical processes we have the main products: nitrogen dioxide and nitric oxide. The secondary products are some nitric acid, the metallic ascorbates, alkyl ascorbates and water.

The gas mixture; nitrogen dioxide, nitric oxide and some impurities.

The gas mixture from the reaction vessel can be drawn away into the gas converter where the gas mixture, the nitric oxide of the gas mixture be converted into nitrogen dioxide by introducing oxygen into the gas converter. Pure oxygen or oxygen in the air will react with nitric oxide to form nitrogen dioxide. From the gas converter the nitrogen dioxide can go out as the final product or can be transferred to the acid converter to produce nitric acid. Also from the gas converter the gas mixture coming from a reaction vessel can go to another system and the two gases, nitrogen dioxide and nitric oxide can be separated by other physical means from each other. Also the two generated gases, nitrogen dioxide and nitric oxide here easily can be separated if that is the intention; the gas mixture from the reaction vessel is transferred into the acid converter, there the gas mixture bubbles through the water; we can say the gas mixture is collected over water, the nitrogen dioxide dissolves into the water there forming nitric acid, plus adds some aggregate amount of nitric oxide to the nitric oxide formed at the chemical reactions in the reaction vessel, and above the solution the nitric oxide collects and it then can be drawn away into the nitrogen-oxide tank and shipped out for further use. Nitric acid produced here is then transferred into the distilling vessel. This way the system can deliver nitric acid and nitric oxide, and the secondary products that come from the reaction vessel.

If the system is designed with a gas tank, the gas mixture is collected in the gas tank, and via the purging line oxygen or air can be introduced into the gas tank. The pure oxygen or oxygen in the air if air is introduced into the gas tank, will react with nitric oxide contained in the gas mixture and thus it will convert into nitrogen dioxide. Now homogeneous nitrogen dioxide can be drawn from the gas tank for other uses or can be transferred into the acid converter where it will bubble through and dissolve into water to form nitric acid and nitric oxide. The nitric oxide collects above the solution and then goes into the nitrogen oxide tank. From the nitrogen oxide tank the gas can be recycled into the system; returned into the gas tank or shipped away for other uses. Also from the gas tank the gas mixture can go to another system where by physical means the gases can be separated or the gas mixture again can be collected under water; this means that the gas mixture is transferred from the gas tank into the acid converter where the gas mixture is bubbled into the water. In the water the nitrogen dioxide forms nitric acid and nitric oxide. The nitric oxide will collect above the solution and then transfers over into the nitrogen-oxide tank; from there the gas can be recycled into the system or shipped away for other uses. The nitric acid again is transferred into the distilling vessel, there the excess water is distilled off and the concentrated nitric acid then transferred into the final nitric acid product tank.

This invention of my is a new way to manufacture nitrogen dioxide, nitric oxide and finally nitric acid. My invention is a new method to produce nitrogen dioxide that is needed as the row material to manufacture nitric acid, and also it is a new way to produce nitric oxide and various metallic and non-metallic ascorbates. This invention makes it possible to produce the eforementioned chemical compounds on small as well as on industrial scale. In this invention to manufacture the eforementioned chemical compounds, one can choose among several nitrite salts as second reactant to use with the ascorbic acid compound to manufacture the desired chemicals: namely, nitrogen dioxide, nitric oxide and then nitric acid and of course the metallic or non-metallic ascorbate. Sure, the reaction rate for the nitrite that can be employed in this process, has a different reaction rate, one is faster than the other, however, all of the nitrite solutions reacting with the ascorbic acid solution, as the surface product of the chemical reactions, are as major products; nitrogen dioxide and nitric oxide that collect above the ascorbic acid solution, metallic ascorbate or alkyl ascorbate and water that remain dissociated in the solution in the reaction vessel, except for silver ascorbate which will precipitate as solid in the reaction vessel in case if silver nitrite is used as the second reactant; in some cases, instead of water, hydrogen is produced. In the liquid phase the chemical reactions give nitric acid, nitric oxide, metallic- or nonmetallic ascorbate, isobutyl ascorbate if isobutyl nitrite is used, and water. The secondary products that come from the reaction vessel from the liquid, these secondary products are the products of the chemical reactions that took place there, these products remain in the solution, except nitric oxide: these are nitric acid, nitric oxide, metallic- or nonmetallic asborbate and water. Nitric oxide collected in the nitrogen-oxide tank can go out of the system as a row material for other uses or recycled back into the gas tank or back into gas-converter.

The secondary products from the reaction vessel are transferred into the secondary distilling vessel that will serve now as a secondary reactor when the system uses sodium nitrite or potassium nitrite or calcium nitrite. At room temperature or at some elevated temperature but not higher than 60 centigrade, sodium bicarbonate is added to solution transferred from the reaction vessel if sodium nitrite was used as the second reactant in the reaction vessel. If potassium nitrite is used as the second reactant, then potassium bicarbonate is added here to the solution. The bicarbonate solid should be added in some excess to the stoichiometric ratio of the unreacted ascorbic acid present in the solution. Adding the solid sodium bicarbonate or potassium bicarbonate or calcium carbonate has the purpose to convert the unreacted ascorbic acid to sodium ascorbate if the second reactant was sodium nitrite or potassium ascorbate if the second reactant was potassium nitrite or calcium ascorbate if the second reactant was calcium nitrite. This process is carried out at 55 to 60° C. Carbon dioxide gas generated in the secondary reaction vessel (26) during the conversion of ascorbic acid to metallic ascorbate is collected in the $CO_2$-tank (94), from the tank the gas can be pumped by a pump (95) into a carry-away container or can be released into the atmosphere via valve (96). Here some of the liquid is also stripped off, and then instead of going into the secondary nitric acid solution tank, it goes into the waste system via valve (111).

The remaining solution and other materials from the secondary distilling vessel are transferred into the settling tank (29). In the settling tank, the metallic, nonmetallic ascorbates precipitate out; it may take some time, then the liquid is either drained or siphoned off or is left to evaporate. The solid ascorbates can then be collected and further purified. The drained liquid may go into the waste-treatment facility.

Of course if one wants to speed up the precipitation of the metallic ascorbates from the secondary solution that was transferred from the reaction vessel (1) into the secondary reaction vessel (26) and the remaining, unreacted ascorbic acid was converted into the appropiate metallic ascorbate and now one wants to pricipitate it out from the solution; the solution from the secondary reaction vessel is transferred into the alcohol-addition vessel (97). In the alcohol-addition vessel (97) to this secondary solution, via line (98) is added 2-propanol. The solution is mixed. From this one solution now two solution layers form. The bottom layer is dark, almost black. With the use of sodium nitrite or potassium nitrite as the second reactant, this black, bottom layer contains most of the secondary product: namely sodium- or potassium ascorbate with some by-products. This sticky, black substance is transferred into the alcohol-addition (97) vessel. Water is added to this solution via water line (101). From this water layer will precipitate the metallic sodium- or potassium ascorbate. This solution from the alcohol-addition vessel (97) can be transferred into the settling tank (29) and let the metallic ascorbate settle out there from the solution and the liquid with the remaining by-products remaining in it drained or siphoned off and carried away via valve (70) to the waste-treatment facility or the solution from the alcohol-addition vessel can be pumped back into the secondary-reaction vessel (26), stripped off some of the liquid, then the remaining solution is transferred into the settling tank (29) and let the metallic ascorbate settle out there; the liquid drained or siphoned off from there, with the by-products in it can be carried away via valve (70) to the waste-treatment facility.

When producing sodium ascorbate with this system, the addition of 2-propanol segments should be avoided, it does not offer really any benefit.

The top layer of the two solutions what we've gotten when we added the 2-propanol to our solution can be checked for product and then pumped over into the alcohol-recovery facility via alcohol-recovery pump (100).

When calcium nitrite is used as the second reactant, calcium ascorbate will be produced as secondary product. This metallic ascorbate can be harvested by addition of 2-propanol. The secondary solution from the secondary-reaction vessel (26) when the reaction of the ascorbic acid and calcium carbonate is over, the solution is transferred into the settling tank (29). Here the yellow precipitate and the unreacted calcium carbonate is separated from the solution. The yellow precipitate may contain some calcium ascorbate, this substance is collected and calcium ascorbate can further be extracted from it. The solution from the settling tank (29) is transferred into the alcohol-addition vessel via pump (102); there 2-propanol is added to the solution via the alcohol-line (98). At addition of 2-propanol to the solution, brown, spongy substance deposits on the bottom of the vessel; this substance is almost like tar, and is removed from the vessel via pump (100). This tar-like substance may contain some calcium ascorbate. The top solution which is brown-whitish, remains in the vessel. This solution contains most or the calcium ascorbate what we intend to isolate. To this solution is added absolute or 95% ethanol via alcohol-line (98); by adding the alcohol, slowly the curdy, white calcium ascorbate precipitate will precipitate out of the solution. This solution now is transferred into the ascorbate-settling tank (99). The solution here goes through filters. The calcium ascorbate remains on the filter bed. However, this compound is very delicate, it should be stabilized, it should be kept for some time in alcohol, then slowly filtered The white solid is then washed with absolute ethanol, then collected under inert gas. The filtrate still contains some calcium ascorbate. This filtrate is collected in ascorbate-filtering tank (102), from there, it is transferred back by pump (103) into the alcohol-addition vessel (97), there again, to this filtrate is added absolute ethanol via alcohol-addition line (98). The solution is mixed well here, and the white calcium ascorbate slowly will precipitate out of the solution. So this solution is transferred into the ascorbate-settling tank, and the same is done with it there as before. The collected calcium ascorbate then can be further purified. The filtrate now goes into the collecting tank via alc. pump (104) or to the recovery system where the alcohols can be recovered.

Potassium ascorbate is not hard to manufacture in this system, but potassium ascorbate as product, it is difficult to precipitate from the mother liquid. A good way to harvest the potassium ascorbate as product from the system to collect it as a mixture of two metallic ascorbates; potassium ascorbate and sodium ascorbate. This mixture is easier to precipitate from solution. Here, from the reaction vessel (1) the secondary solution is transferred into the secondary-reaction vessel (26); to this solution sodium bicarbonate is added from the carbonate-delivery system (105), the solution is heated up to 55° and maintained at that temperature until the chemical reaction is over. The released carbon dioxide gas forming during the reaction goes into the $CO_2$-tank (94). Once the chemical reaction is over, some of the liquid of the solution here is stripped off, then the solution from the secondary-reaction vessel (26) is transferred into the settling tank (29), the mixture of potassum ascorbate and sodium ascorbate is left on the filter bed to precipitate, the precipitate is washed with absolute ethanol, collected, then can be further purified. The filtrate via valve (70) goes to the waste-recovery facility.

In my invention the chemical reactions take place in the reaction vessel FIG. 1; apparatus (1). The ascorbic acid solution is loaded into the reaction vessel via the load line (2). The ascorbic acid solution makes a shallow pool in the reaction vessel (1) and is mechanically mixed by the mixer (3). The second reactant, the nitrite salt solution; be it sodium nitrite, potassium nitrite, calcium nitrite, barium nitrite, isobutyl nitrite etc.; nitrite solution is interjected into the reaction vessel (1) via the acid-delivery line (4) onto which the acid-shower heads (5) are mounted. The second reactant, through the acid-shower heads, is sprayed onto the surface of the ascorbic acid solution pool. As the reactants come into contact with each other in the reaction vessel, the formed gas mixture from the surface reaction that is nitrogen dioxide, nitric oxide and some impurity gases, collect on the surface of the solution pool. The generated gases are sucked away either into the gas converter (7) or it is left to drift over into the gas tank (8) if the system is designed with a gas tank through the gas-line (6). The gas-line has a one-directional (9) valve to prevent the gas flowing back into the reaction vessel. There is a vacuum line (10) joined to it. In the gas converter (7) the gas mixture that is nitrogen dioxide and nitric oxide. Nitric oxide is converted into nitrogen dioxide by addition of oxygen under pressure to the gas mixture. The oxygen is introduced into the gas converter via the oxygen-line (11). The same can be done when the gas mixture is collected in the gas tank (8). The oxygen is introduced into the gas tank via the purging line (12). The gas mixture is mixed and all the nitric oxide is converted into nitrogen dioxide. From the gas converter (7) or gas tank (8) nitrogen dioxide can be used as final product and shipped out of the system or transferred into the acid converter (14). Acid converter (14) is filled with water via the water-line (15). The nitrogen dioxide is bubbled into the water; the nitrogen dioxide gas reacts with water proportionately forms nitric acid and nitrogen oxide. In the acid converter (14) the solution is mixed. The formed nitric acid remains in the solution and the nitric oxide collects on the surface and drifts over or can be transferred over into the nitrogen-oxide tank (17); there the gas is collected and can be shipped away for other use or recycled back via the NO-gas-recycling line (18). From the acid converter (14) nitric acid solution is transferred into the distilling vessel (20); there the water is distilled off, then the concentrated nitric acid is pumped through the nitric acid cooler (22) where the acid is cooled, into the nitric acid product tank. The distilled off water is cooled in the water cooler (24), then it goes out of the system. If the intent is to produce (collect) nitric oxide, then the gas mixture from the reactor vessel (1) goes, not reacting with oxygen, straight into the acid converter (14), there the gas mixture is treated as before, however, this time the system produces more nitric oxide and less nitric acid.

The secondary products from the reaction vessel (1); as water, some nitric acid, metallic ascorbate or alkyl ascorbate, ascorbic acid solution are transferred by the secondary product pump (25) into the secondary-reaction vessel (26); here the remaining, unreacted ascorbic acid is converted into metallic ascorbate by addition of sodium bicarbonate or potassium bicarbonate or calcium carbonate via the carbonate-delivery system (105). The carbon dioxide gas generated by the chemical reaction is carried away from the secondary reaction vessel via the carbon-dioxide collecting system (94). Once the chemical reactions are over, the solution from the secondary-reaction vessel is transferred into the settling tank (29); there the metallic ascorbate or alkyl ascorbate precipitates out of the solution, then is collected and further purified. The collected filtrate goes to the waste-recovery facility via valve (70).

If alcohol is used to precipitate the metallic ascorbate, once the chemical reactions are over, the solution from the secondary-reaction vessel (26) is pumped over into the alcohol-addition vessel (98). In the alcohol-addition vessel, 2-propanol is added to the transferred solution; by this act two solution layers form. The bottom layer is dark, and it contains most of the metallic ascorbate product. This dark, bottom layer solution is transferred into the ascorbate tank (99) via transfer-pump B (107), there water is added to the solution via water-line (108). Now this solution is pumped over by the solution pump (109) into the secondary-reaction vessel (26). Some of the liquid of this solution is stripped off here via strip-off line (110), and the stripped off liquid goes via valve (111) to the waste-recovery facility. Now from the secondary-reaction vessel the solution is transferred into the settling tank (29). In the settling tank the metallic ascorbate there settles out of the solution on the filtering bed; the metallic ascorbate is collected and further purified. The filtrate goes via valve (70) into the waste-recovery facility.

The top layer solution from the alcohol-addition vessel (97) is pumped out by the alcohol-recovery pump into the alcohol-recovery system.

The above described processes in this industrial as well as in laboratory system can be run with isoascorbic acid as the first reactant, all the processes, chemical reactions will be the same or fairly the same; the chemical reactions, however, will be slower, and of course ascorbate products with isoascorbate as first reactant, will be isoascorbates.

This chemical manufacturing system in my invention has its safety feature. It has the water tank (30). The water tank (30) is filled with water by the water pump (31) from the water supply. The water tank (30) is joined to the reaction vessel (1) through the safety line (32). At the end of the reaction vessel there is a safety membrane (33) on the safety line. If the pressure raises in the reaction vessel above its safety level, the safety membrane will break, the gas mixture will pour over from the reaction vessel (1) into the water tank (30); nitrogen dioxide dissolves into water forming nitric acid, nitric oxide collects then into the gas-safety tank (33). Gas-safety tank (33) is connected to the gas-mixture line (6). The safety tank (30) also is connected to the gas tank (8) with the gas-tank-safety line (35); at the end of the line, in the gas tank (8) also is a safety membrane (36); the safety membrane will burst if the pressure in the gas tank (8) raises above the safety limit and the gas will pour over into the water tank (30) and the same chemical, mechanical processes will take effect as they have been described at the reaction vessel (1) safety features.

The reaction vessel (1) has pressure control (37), temperature control (38), level control (39), sample valve (40), water cooling system (41).

Water tank (30) has a pressure control (42), temperature control (43), level control (44), safety valve (45), waste line (46).

Gas tank (8) has a mixer (47), pressure control (48), temperature control (49), pressure gauge (50), level control (51), water cooling (53).

The secondary distilling vessel (26) has a safety valve (55), pressure control (56), temperature control (57), level control (58), purging line (59), sample line (60).

Settling tank (29) has a level control (69), waste line (70).

Acid converter has a pressure control (71), level control (72), temperature control (73), sample valve (74), waste line (75), water-cooling system (76).

Nitrogen-oxide tank (17) has a safety valve (77), pressure control (78), temperature control (79).

Distilling vessel (20) has a mixer (80), pressure control (81), temperature control (82), 1level control (83), steam line (84), sample valve and waste line (85).

Water cooler (24) has sample valve (86).

Nitric acid product-tank (23) has a safety valve (87), pressure control (88), temperature control (89), level control (90), sample valve (91), shipping-line (92), waste-line (93).

Gas-tank (8) can be used as acid converter (14) too. Water can be pumped into it via the purging-line (12). In smaller systems the acid converter can be omitted then.

The invention claimed is:

1. A process for preparing nitrogen dioxide, nitric oxide and calcium ascorbate or calcium isoascorbate comprising reacting aqueous ascorbic acid solution or aqueous isoascorbic acid solution with aqueous calcium nitrite in a reaction vessel at a temperature of about 25° C.

* * * * *